United States Patent
Mankodi et al.

(10) Patent No.: US 12,364,902 B2
(45) Date of Patent: Jul. 22, 2025

(54) LOGIC FOR MODULATING ENTRAINMENT SEQUENCE WITH BIOFEEDBACK

(71) Applicant: BOSE CORPORATION, Framingham, MA (US)

(72) Inventors: Harsh A. Mankodi, Brighton, MA (US); David Rolland Crist, Watertown, MA (US); Joseph Rossi, Jamaica Plain, MA (US); Sara Adkins, Allston, MA (US); Chia-Ling Li, Framingham, MA (US); Navaneethan Sivagnanasundaram, Waltham, MA (US); Kathleen Elizabeth Kremer, Southborough, MA (US)

(73) Assignee: Bose Corporation, Framingham, MA (US)

( * ) Notice: Subject to any disclaimer, the term of this patent is extended or adjusted under 35 U.S.C. 154(b) by 1018 days.

(21) Appl. No.: 17/420,427

(22) PCT Filed: Jan. 6, 2020

(86) PCT No.: PCT/US2020/012371
§ 371 (c)(1),
(2) Date: Jul. 2, 2021

(87) PCT Pub. No.: WO2020/146259
PCT Pub. Date: Jul. 16, 2020

(65) Prior Publication Data
US 2022/0080258 A1    Mar. 17, 2022

Related U.S. Application Data (60) Provisional application No. 62/789,380, filed on Jan. 7, 2019.

(51) Int. Cl.
*A63B 23/18*    (2006.01)
*A63B 71/06*    (2006.01)

(52) U.S. Cl.
CPC ........ *A63B 23/185* (2013.01); *A63B 71/0622* (2013.01); *A63B 2071/0663* (2013.01);
(Continued)

(58) Field of Classification Search
CPC .......................... A63B 23/185; A63B 71/0622
See application file for complete search history.

(56) References Cited

U.S. PATENT DOCUMENTS

| 2006/0102171 A1 | 5/2006 | Gavish |
| 2009/0024047 A1 | 1/2009 | Shipley et al. |

(Continued)

FOREIGN PATENT DOCUMENTS

| EP | 0856334 A2 | 8/1998 |
| GB | 2567678 A | 4/2019 |

OTHER PUBLICATIONS

International Search Report and Written Opinion for International Application No. PCT/US2020/012371 Dated Apr. 15, 2020.
(Continued)

*Primary Examiner* — Kesha Frisby
(74) *Attorney, Agent, or Firm* — Patterson + Sheridan, LLP (57) ABSTRACT

Aspects of the present disclosure provide methods, apparatuses, and systems for non-linear breathing entrainment. According to an aspect, a final breathing period is selected, and a current breathing period of a user is measured. A guiding stimulus configured to alter the current breathing period towards the final breathing period over an interval of time at a non-linear prescribed rate is output. A difference between the current breathing period and a target breathing period along the non-linear linear prescribed rate is determined. Based at least in part on the difference, the guiding stimulus and/or the non-linear prescribed rate are adjusted. The guiding stimulus and the non-linear prescribed rate may
(Continued)

be stabilized, increased, or decreased to enable the user to reach the final breathing period.

21 Claims, 5 Drawing Sheets

(52) U.S. Cl.
CPC ..... *A63B 2220/40* (2013.01); *A63B 2220/808* (2013.01); *A63B 2220/89* (2013.01); *A63B 2225/20* (2013.01); *A63B 2225/50* (2013.01); *A63B 2230/425* (2013.01)

(56) References Cited

U.S. PATENT DOCUMENTS

| | | |
|---|---|---|
| 2016/0151603 A1 | 6/2016 | Shouldice |
| 2017/0173298 A1 | 6/2017 | Benway et al. |
| 2018/0078735 A1 | 3/2018 | Dalgleish et al. |
| 2020/0215383 A1* | 7/2020 | Mankodi .............. A61B 5/0816 |

OTHER PUBLICATIONS

Bumatay, Antionette, et al., "Investigating the Role of Biofeedback and Haptic Stimulation in Mobile Paced Breathing Tools", International Conference on Financial Cryptography and Data Security, May 18, 2017.

"Linear Function." Wikipedia, https://en.wikipedia.org/wiki/Linear_function, Retrieved on Aug. 30, 2024.

* cited by examiner

LOGIC FOR MODULATING ENTRAINMENT SEQUENCE WITH BIOFEEDBACK

CROSS-REFERENCE TO RELATED APPLICATIONS

This application is a national stage application under 35 U.S.C. 371 of PCT/US2020/012371, filed Jan. 6, 2020, which claims priority to and benefit of U.S. Patent Application No. 62/789,380, filed Jan. 7, 2019, the contents of which are herein incorporated by reference in their entirety.

FIELD

Aspects of the present disclosure generally relate to methods, apparatuses, and systems for non-linear breathing entrainment.

BACKGROUND

Utilizing breathing entrainment to regulate a user or subject's breathing rate, or amount of breaths taken per minute, can be beneficial in a number of health fields. For example, breathing entrainment can be used in several clinical applications, potentially leading to more effective or quicker treatments of conditions, including: asthma, stress, anxiety, insomnia, panic disorder, recurrent abdominal pain, chronic obstructive pulmonary disease, chronic hyperventilation, hypertension, and congestive heart failure, among others. Breathing entrainment may also be utilized to assist people in falling asleep and for meditation or relaxation purposes.

Typical breath entrainment schemes modulate a user's actual breath rate in breaths per minute. In certain cases, a target rate is provided as a steady stimulus for the entire duration of the entrainment scheme. This involves effort by the user, as the user has to manage their breathing to match that stimulus. Another breath entrainment scheme decreases a user's amount of breaths per minute in a linear or step-wise manner by reducing the amount of breaths taken per minute by one full breath. For instance, if a user follows the breathing entrainment sequence for one minute taking 9 breaths per minute, the next reduction is to 8 breaths per minute, and so on. This type of breathing entrainment sequence may be uncomfortable for some users, being too unnatural and difficult to follow. Additionally, if a user fails to follow or accurately keep up with the breathing entrainment sequence, it can be difficult for the user to catch back up to the quick pace of the sequence. Therefore, there is a need for a breathing entrainment method that is easier for users to follow and complete.

SUMMARY

Aspects of the present disclosure provide methods, apparatuses, and systems for non-linear breathing entrainment. As described herein, "entrainment" and "breathing entrainment" refer to guiding a user's breath or breathing. According to an aspect, a final breathing period is selected, and a current breathing period of a user is measured. A guiding stimulus configured to alter the current breathing period towards the final breathing period over an interval of time at a non-linear prescribed rate is output. A difference between the current breathing period and a target breathing period along the non-linear prescribed rate is determined. Based at least in part on the difference, the guiding stimulus and/or the non-linear prescribed rate are adjusted. The guiding stimulus and the non-linear prescribed rate may be stabilized, increased, or decreased to enable the user to reach the final breathing period.

In an aspect, a method for breathing entrainment comprises selecting a final breathing period. A breathing period is an amount of time from a beginning of one inhale to an end of a next exhale. The method further comprises measuring a current breathing period of a user and outputting a guiding stimulus. The guiding stimulus is configured to alter the current breathing period towards the final breathing period over an interval of time at a non-linear prescribed rate. The method further comprises determining a difference between a target breathing period and the current breathing period. The target breathing period is the breathing period the user should be at along the non-linear prescribed rate at a certain point of time. The method further comprises adjusting the guiding stimulus based at least in part on the difference between the target breathing period and the current breathing period.

Determining the difference between the target breathing period and the current breathing period may comprise determining the difference exists for a predetermined amount of time prior to adjusting the guided stimulus. Determining the difference between the target breathing period and the current breathing period may comprise determining the difference exceeds a first threshold. The difference exceeding the first threshold may indicate the current breathing period of the user is predicted to reach the final breathing period faster than the non-linear prescribed rate, and the guiding stimulus and the non-linear prescribed rate may be decreased to match the current breathing period of the user.

The difference exceeding the first threshold may indicate the current breathing period of the user is predicted to reach the final breathing period slower than the non-linear prescribed rate, and the guiding stimulus and the non-linear prescribed rate may be stabilized to allow the current breathing period of the user to align to the guiding stimulus and the non-linear prescribed rate.

The method may further comprise determining the difference between the target breathing period and the current breathing period exceeds a second threshold greater than the first threshold. The difference exceeding the second threshold may indicate the current breathing period of the user is predicted to reach the final breathing period slower than the non-linear prescribed rate, and the guiding stimulus and the non-linear prescribed rate may be increased to match the current breathing period of the user.

The method may further comprise determining the difference between the target breathing period and the current breathing period does not exceed a first threshold. The guided stimulus may be adjusted at the non-linear prescribed rate.

In another aspect, a wearable audio device comprises at least one biosensor for measuring a current breathing period of the user wearing the wearable audio device. A breathing period is an amount of time from a beginning of one inhale to an end of a next exhale. The wearable audio device further comprises at least one speaker configured to output a guiding stimulus. The guiding stimulus is configured to alter the current breathing period towards a final breathing period over an interval of time at a non-linear prescribed rate. The wearable audio device further comprises a processing unit or processor configured to select the final breathing period and determine a difference between a target breathing period and the current breathing period. The target breathing period is the breathing period the user should be at along the non-linear prescribed rate at a certain point of time. The processing unit is further configured to adjust the guiding stimulus based at least in part on the difference between the target breathing period and the current breathing period.

The processing unit may be further configured to determine the difference exists for a predetermined amount of time prior to adjusting the guided stimulus. The processing unit may be further configured to determine the difference exceeds a first threshold. The difference exceeding the first threshold may indicate the current breathing period of the user is predicted to reach the final breathing period faster than the non-linear prescribed rate, and the guiding stimulus and the non-linear prescribed rate may be decreased to match the current breathing period of the user.

The difference exceeding the first threshold may indicate the current breathing period of the user is predicted to reach the final breathing period slower than the non-linear prescribed rate, and the guiding stimulus and the non-linear prescribed rate may be stabilized to allow the current breathing period of the user to align to the guiding stimulus and the non-linear prescribed rate.

The processing unit may be further configured to determine the difference between the target breathing period and the current breathing period exceeds a second threshold greater than the first threshold. The difference exceeding the second threshold may indicate the current breathing period of the user is predicted to reach the final breathing period slower than the non-linear prescribed rate, and the guiding stimulus and the non-linear prescribed rate may be increased to match the current breathing period of the user.

The processing unit may be further configured to determine the difference between the target breathing period and the current breathing period does not exceed a first threshold. The guided stimulus may be adjusted at the non-linear prescribed rate.

In yet another aspect, an audio system comprises at least one biosensor for measuring a current breathing period of the user wearing the wearable audio device. A breathing period is an amount of time from a beginning of one inhale to an end of a next exhale. The audio system further comprises at least one speaker configured to output a guiding stimulus. The guiding stimulus is configured to alter the current breathing period towards a final breathing period over an interval of time at a non-linear prescribed rate. The audio system further comprises a processing unit configured to select the final breathing period and determine a difference between a target breathing period and the current breathing period. The target breathing period is the breathing period the user should be at along the non-linear prescribed rate at a certain point of time. The processing unit is further configured to adjust the guiding stimulus based at least in part on the difference between the target breathing period and the current breathing period.

The processing unit may be further configured to determine the difference exists for a predetermined amount of time prior to adjusting the guided stimulus. The processing unit may be further configured to determine the difference exceeds a first threshold. The difference exceeding the first threshold may indicate the current breathing period of the user is predicted to reach the final breathing period faster than the non-linear prescribed rate, and the guiding stimulus and the non-linear prescribed rate may be decreased to match the current breathing period of the user.

The difference exceeding the first threshold may indicate the current breathing period of the user is predicted to reach the final breathing period slower than the non-linear prescribed rate, and the guiding stimulus and the non-linear prescribed rate may be stabilized to allow the current breathing period of the user to align to the guiding stimulus and the non-linear prescribed rate.

The processing unit may be further configured to determine the difference between the target breathing period and the current breathing period exceeds a second threshold greater than the first threshold. The difference exceeding the second threshold may indicate the current breathing period of the user is predicted to reach the final breathing period slower than the non-linear prescribed rate, and the guiding stimulus and the non-linear prescribed rate may be increased to match the current breathing period of the user.

The processing unit may be further configured to determine the difference between the target breathing period and the current breathing period does not exceed a first threshold. The guided stimulus may be adjusted at the non-linear prescribed rate.

All examples and features mentioned herein can be combined in any technically possible manner.

DETAILED DESCRIPTION

Figure 1:
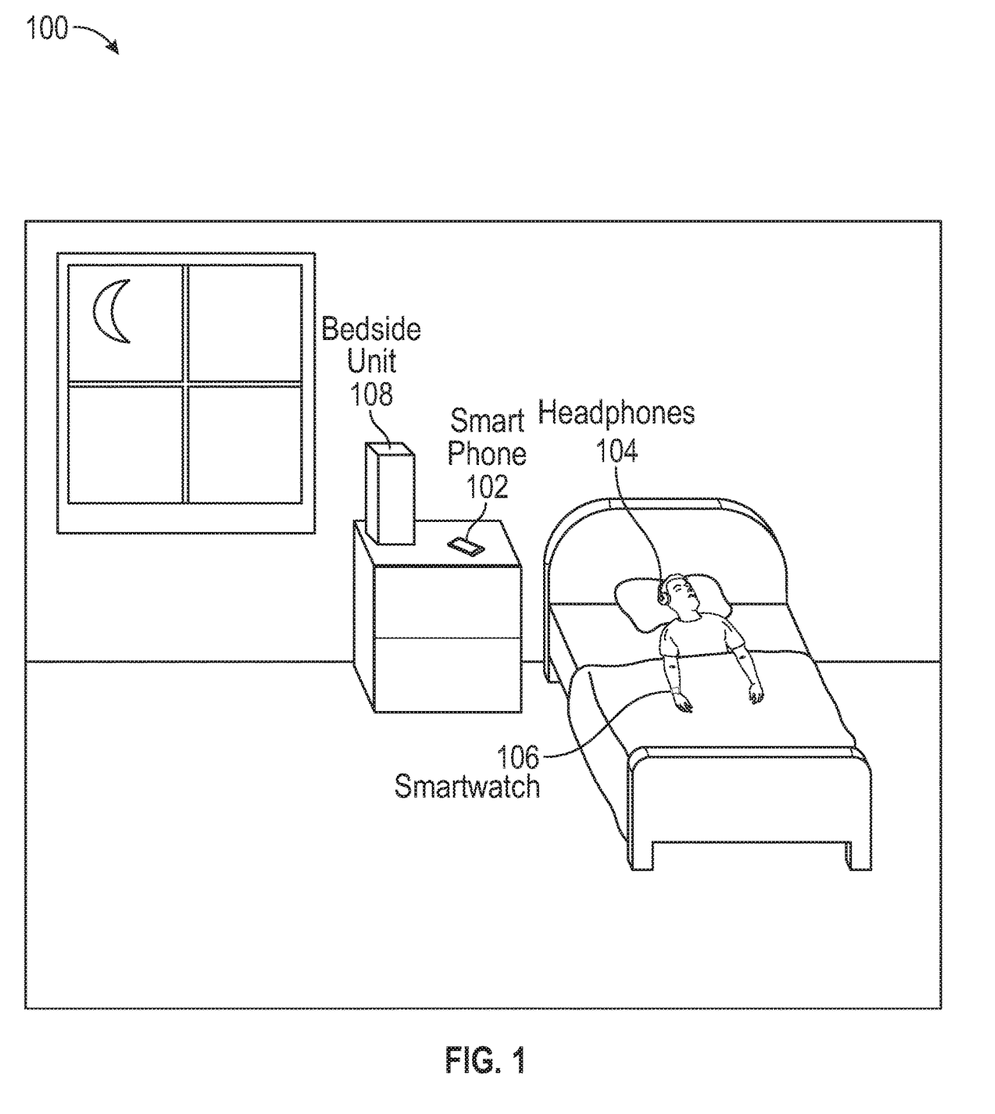
FIG. 1 illustrates an example audio system in a sleeping environment.

FIG. 1 illustrates an example audio system 100 in a sleeping environment, according to an aspect. The audio system 100 may be used to determine a difference between a target breathing period and a current breathing period, and adjust a guiding stimulus along a non-linear prescribed rate based at least in part on the difference between the target breathing period and the current breathing period to correct errors that occur during in a non-linear breath entrainment sequence. As described herein, "entrainment" refers to guiding a user's breath or breathing.

The audio system 100 includes headphones 104 and a smartwatch 106, which are shown as being worn by a subject or user. A headphone 104 refers to a device that fits around, on, or in an ear and that radiates acoustic energy into the ear canal. Headphones 104 are sometimes referred to as earphones, earpieces, headsets, earbuds, or sport headphones, and can be wired or wireless. The headphones 104 may comprise one or more of: a processing unit, a transceiver, one or more biosensors, one or more speakers, and one or more microphones. The headphones 104 may comprise an interface configured to receive input from a subject or user. A smartwatch 106 may be any type of wearable computer designed to be worn on a wrist of a subject or user, such as a fitness tracker. The smartwatch 106 may comprise one or more of: a processing unit, a transceiver, one or more biosensors, one or more speakers, and one or more microphones. The smartwatch 106 may comprise an interface configured to receive input from a subject or user.

The audio system 100 further includes a bedside unit 108 and a smartphone 102. The smartphone 102 may be a mobile phone, tablet, phablet, or laptop computer. The smartphone 102 may comprise one or more of: a processing unit, a transceiver, one or more biosensors, one or more speakers, and one or more microphones. The smartphone 102 may comprise an interface configured to receive input from a subject or user. The bedside unit 108 may be a stationary smart device, such as a smart speaker. The bedside unit 108 may have any shape and size capable of fitting on a surface in the sleeping environment, such as a dresser, desk, or night table. The bedside unit 108 may comprise one or more of: a processing unit, a transceiver, one or more biosensors, one or more speakers, and one or more microphones. In one embodiment, the bedside unit 108 comprises one or more contactless biosensors, such as a radio frequency (RF) sensor, a radar sensor, or an under-bed accelerometer. The bedside unit 108 may comprise an interface configured to receive input from a subject or user.

The headphones 104, the smartwatch 106, the bedside unit 108, and the smartphone 102 may each include any wired or wireless communication means suitable for use with any other device 102-108 disposed in the sleeping environment, such as WiFi, Bluetooth, Near Field Communications (NFC), USB, micro USB, or any suitable wired or wireless communications technologies known to one of ordinary skill in the art. For example, the headphones 104 may comprise one or more speakers while the bedside unit 108 comprises one or more biosensors in communication with the one or more speakers of the headphones 104. Furthermore, the audio system 100 may include one or more of the devices 102-108, and is not required to include each device 102-108 shown. Thus, each device 102-108 in the audio system 100 may be optionally included, and only one device 102-108 is needed to determine and correct errors in a non-linear breathing entrainment sequence.

The devices 102-108 of the audio system 100, either alone or in combination, are configured to: select the final breathing period, to measure a current breathing period of the user, output a guiding stimulus, the guiding stimulus being configured to alter the current breathing period towards a final breathing period over an interval of time at a non-linear prescribed rate, determine a difference between a target breathing period and the current breathing period, the target breathing period being the breathing period the user should be at along the non-linear prescribed rate at a certain point of time, and adjust the guiding stimulus based at least in part on the difference between the target breathing period and the current breathing period.

Figure 2:
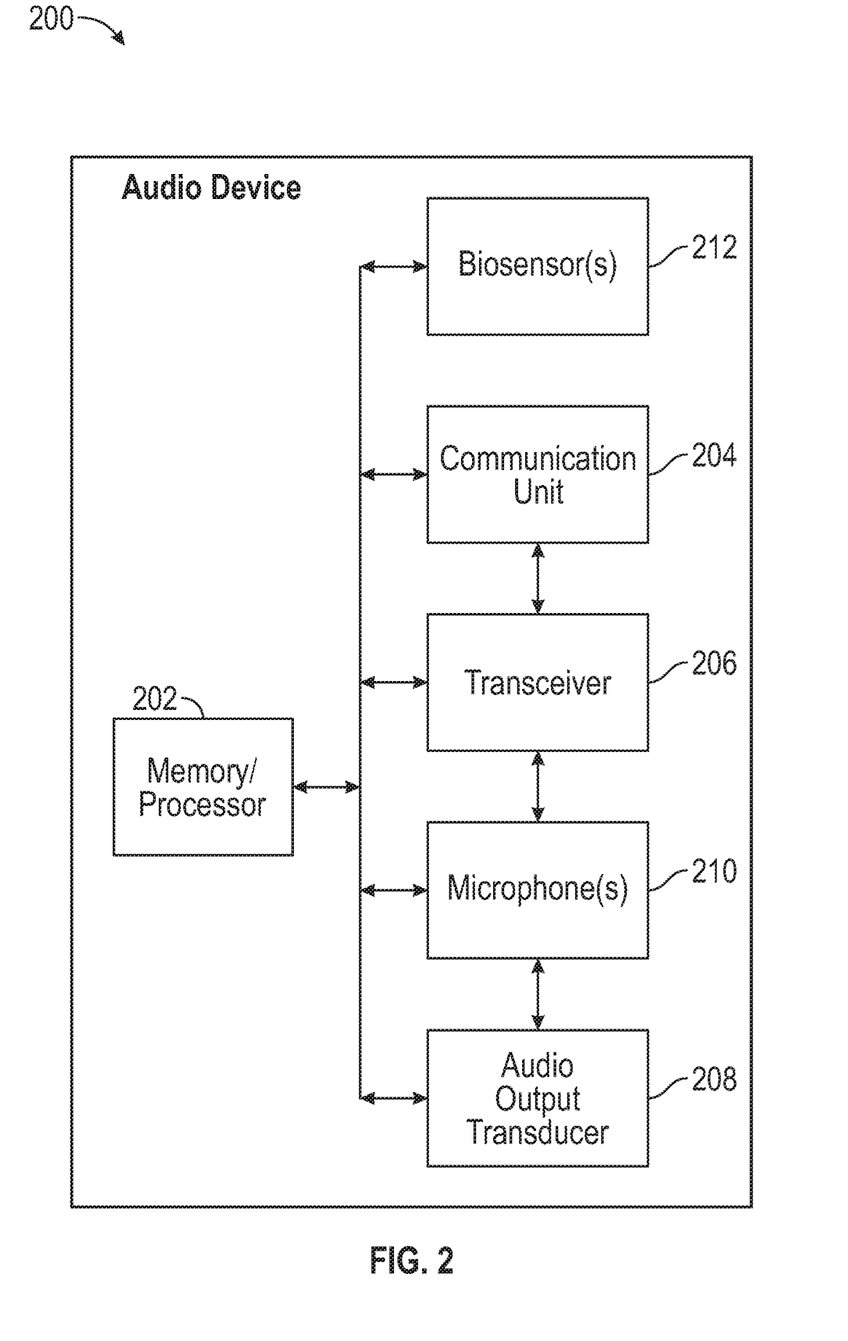
FIG. 2 illustrates example components of an audio device.

FIG. 2 illustrates example components of an audio device 200, in accordance with certain aspects of the present disclosure. According to an example, the audio device 200 is a wireless wearable audio device. The audio device 200 may be used in an audio system, such as the audio system 100 of FIG. 1. For instance, the audio device 200 may be any device 102-108 in the audio system 100 of FIG. 1. In one example, the audio device 200 is the headphones 104 of FIG. 1. In another example, the audio device 200 is the bedside unit 108 of FIG. 1. The audio device 200 may be used to determine a difference between a target breathing period and a current breathing period, and adjust a guiding stimulus along a non-linear prescribed rate based at least in part on the difference between the target breathing period and the current breathing period to correct errors that occur during in a non-linear breath entrainment sequence.

The audio device 200 includes a memory and processor (or processing unit) 202, communication unit 204, a transceiver 206, a biosensor 212, and an audio output transducer or speaker 208. The memory may include Read Only Memory (ROM), a Random Access Memory (RAM), and/or a flash ROM. The memory stores program code for controlling the memory and processor 202. The memory and processor 202 control the operations of the audio device 200. Any or all of the components in FIG. 2 may be combined into multi-function components.

The processor 202 controls the general operation of the audio device 200. For example, the processor 202 performs process and control for audio and/or data communication. The processor 202 is configured to measure, receive, calculate, or detect at least one biosignal parameter of the subject. In combination with the audio output transducer 208, the processor 202 is configured to output the guiding stimulus. The processor 202 is further configured to determine one or more errors or differences in a non-linear breath entrainment and to alter the guiding stimulus. The processor 202 may be further configured to receive input from a subject or user, such as input regarding an initial breath rate per minute and a final breath rate per minute. In at least one example, the processor 202 is disposed on another device in an audio system, such as a smartphone, and is in communication with the audio device 200.

The communication unit 204 facilitates a wireless connection with one or more other wireless devices, such as with other devices in an audio system. For example, the communication unit 204 may include one or more wireless protocol engines such as a Bluetooth engine. While Bluetooth is used as an example protocol, other communication protocols may also be used. Some examples include Bluetooth Low Energy (BLE), NFC, IEEE 802.11, WiFi, or other local area network (LAN) or personal area network (PAN) protocols. The audio device 200 may receive audio files wirelessly via the communication unit 204. Additionally or alternatively, the communication unit 204 may receive information associated with a subject's biosignal parameters, obtained via a contactless sensor. Examples of contactless sensors include a RF sensor, a radar sensor, or an under-bed accelerometer.

The transceiver 206 transmits and receives information via one or more antennae to exchange information with one or more other wireless devices. The transceiver 206 may be used to communicate with other devices in an audio system, such as a bedside unit, a smartphone, and/or a smartwatch. The transceiver 206 is not necessarily a distinct component.

The audio device 200 includes the audio output transducer 208, which may be also known as a driver or speaker. In some examples, more than one output transducer 208 is used. The transducer 208 (that may be part of a microphone) converts electrical signals into sound and converts sound into electrical signals. The transducer 208 is configured to output a guiding stimulus to a user or subject. The transducer 208 outputs audio signals, including adjusted audio signals in an effort to regulate a subject or user's breathing. For example, the transducer 208 may be configured to adjust audio signals in response to a subject's biosignal parameters. In at least one example, the transducer 208 is disposed on another device in an audio system, such as a bedside unit, and is in communication with the audio device 200.

The audio device 200 optionally includes one or more microphones 210. In an aspect, the microphones 210 are used to convert noises into electrical signals. In at least one example, one or more microphones 210 are disposed on another device in an audio system, such as a bedside unit, and are in communication with the audio device 200. The microphone 210 may be used to approximate or measure a user's breath rate per minute.

The audio device 200 optionally includes one or more biosensors 212 used to determine, sense, measure, monitor, or calculate a biosignal parameter of a subject wearing the audio device 200.

According to an aspect when the audio device 200 is headphones, only one earpiece (ear tip, ear cup) of the audio device 200 includes the biosensor 212. In an aspect, neither earpiece includes a biosensor 212. Instead, a biosensor not on the audio device 200, may remotely detect a biosignal parameter of the subject. In an example, the biosensor 212 detects a subject's heartrate or heart rate variability (HRV) with a sensor disposed on the wrist, such as by utilizing a smartwatch. In an example, the biosensor 212 may be a contactless biosensor. The contactless biosensor is configured to report detected biosignal parameters to the processor 202, for example, via the communication unit 204. In at least one example, the biosensor 212 is disposed on another device in an audio system, such as a smartwatch, and is in communication with the audio device 200.

FIG. 2 illustrates communication between certain modules of an example audio device 200; however, aspects of the disclosure are not limited to the specific illustrated example. According to aspects, any module 202-212 is configured to communicate with any other module in the audio device 200. In one example, all modules 202-212 are connected to and communicate with each other.

Figure 3:
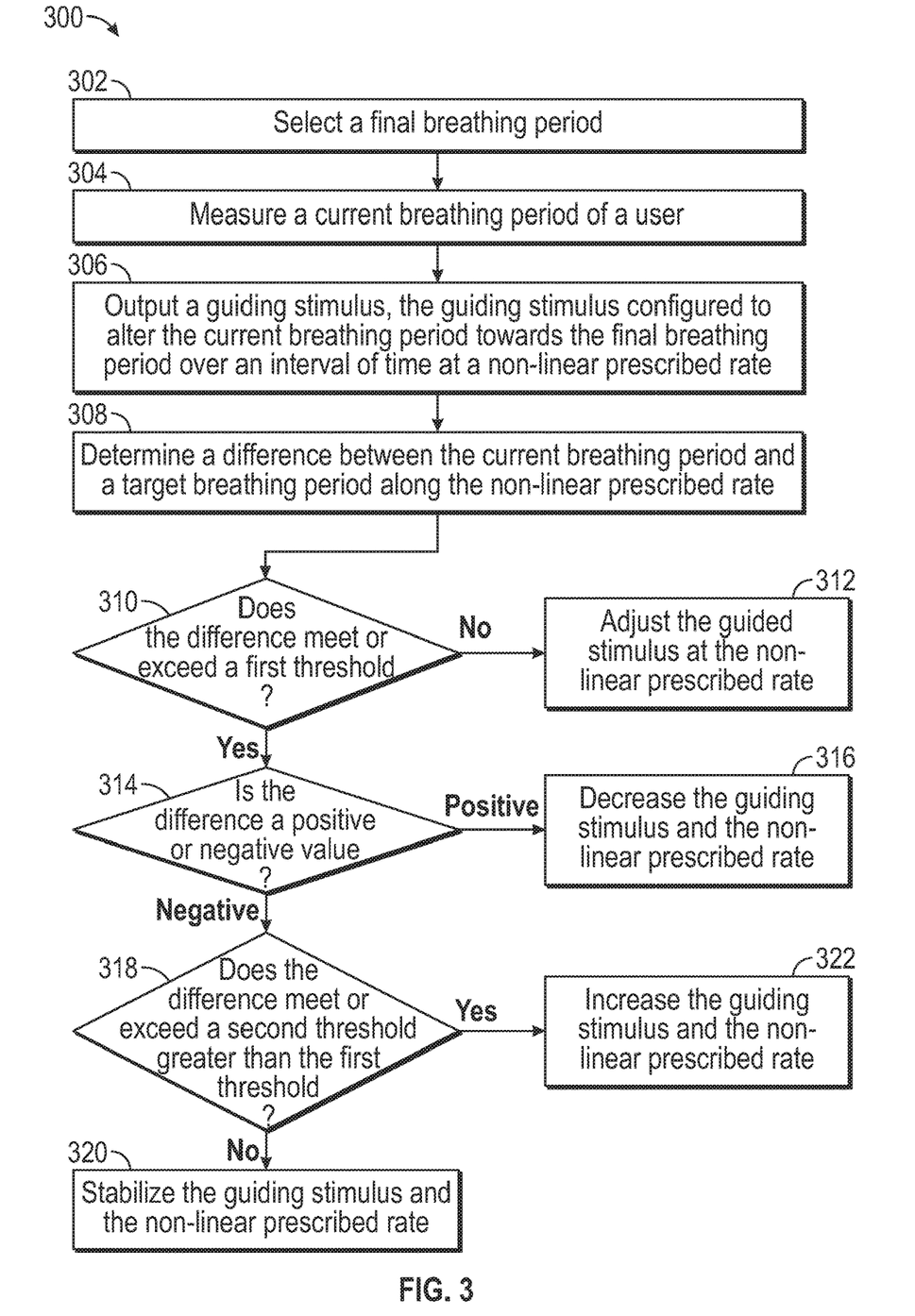
FIG. 3 illustrates an example method for breathing entrainment.

FIG. 3 illustrates an example method 300 for non-linear breathing entrainment, according to one embodiment. Method 300 may be implemented utilizing the audio system 100 of FIG. 1 and/or the audio device 200 of FIG. 2.

In 302, a final breathing period is selected. A breathing period is an amount of time from a beginning of one inhale to an end of a next exhale. A final breathing period is the desired breathing period after the breathing entrainment has been completed. The final breathing period may be selected by a user, or may be preset or predetermined. An example of a final breathing period is about a 10 second breathing period or about 6 breaths per minute.

In 304, a current breathing period of a user is measured. The current breathing period of a user is measured using a biometric sensor, such as the biosensor 212 of FIG. 2. The current breathing period may further be measured or approximated using a microphone, such as the microphone 210 of FIG. 2. The current breathing period is generally higher than the target breathing period, such as about a 6 second breathing period or about 10 breaths per minute. In one embodiment, the current breathing period is measured when method 300 begins to determine an initial breathing period. The current breathing period may then be measured one or more times during the entrainment sequence.

In 306, a guiding stimulus is output. The guiding stimulus is configured to alter the current breathing period of the user towards the final breathing period over an interval of time at a non-linear prescribed rate. The guiding stimulus may be a pre-produced sound or pre-produced soundtrack. The non-linear prescribed rate is a predetermined breathing entrainment rate or sequence that starts at the initial breathing period and ends at the final breathing period. In other words, the non-linear prescribed rate extends from the initial breathing period to the final breathing period over a total time of entrainment. The total time of entrainment is the amount of time the breathing entrainment sequence or exercise lasts. The non-linear prescribed breathing rate may be a non-linear decay. The non-linear prescribed rate may not follow a step-wise or linear function (e.g., decreasing by one breath per minute). The non-linear prescribed rate may be governed by the inverse of the breathing period, as shown by Equation 1:

$$Rate_{Breath} = \frac{60 \text{ seconds}}{Period} \quad \text{Equation 1}$$

In 308, a difference between a target breathing period and the current breathing period is determined. A target breathing period is the targeted breathing period the user should be at along the non-linear prescribed rate at a certain point of time in the breathing entrainment sequence. The difference is utilized to determine an error amount, if any, of how far off the user or subject is from the non-linear prescribed rate. The difference or error is calculated in seconds, and may be a positive or negative number. The difference or error is governed by Equation 2:

Equation 2: $Error = Period_{current} - Period_{Target}$

The error being a positive number generally indicates the user is leading ahead of the non-linear prescribed rate. The user leading the entrainment means the user's breathing is slower or longer than the target breathing period. The error being a negative number generally indicates the user is lagging behind the non-linear prescribed rate. The user lagging in entrainment means the user's breathing is faster or shorter than the target breathing period. For example, after following the breathing entrainment sequence for about 3 minutes, the target breathing period is about 6.81 seconds (about 8.8 breaths per minute), but the user has a current breathing period of about 6.52 seconds (about 9.2 breaths per minute). In such an example, the difference or error is −0.29 seconds, indicating the user is lagging or behind the non-linear prescribed rate by 0.29 seconds. In one embodiment, Equation 2 is reversed such that the error equals the target breathing period minus the current breathing period. In such an embodiment, a positive number would indicate the user is lagging behind the non-linear prescribed rate, and a negative number would indicate the user is leading the non-linear prescribed rate.

In 310, a determination is made as to whether the difference between the target breathing period and the current breathing period meets or exceeds a first threshold. The first threshold may be a positive or negative number depending on whether the user is leading or lagging behind the non-linear prescribed rate. In one embodiment, the first threshold is about ±0.5 seconds. In such an embodiment, if the user is lagging, the first threshold is about −0.5 seconds, and if the user is leading, the first threshold is about 0.5 seconds.

The system may optionally determine whether the difference exists for a predetermined buffer time. The predetermined buffer time may be between about 15-45 seconds. In a specific example, the predetermined buffer is between about 20-40 seconds. In such an embodiment, if the difference does exist for the predetermined buffer time, method 300 then proceeds on to either 312 or 314. If the difference does not exist for the predetermined buffer time, method 300 restarts at 304 and re-measures the current breathing period of the user.

If the difference does not exceed the first threshold, the guided stimulus is adjusted at the non-linear prescribed rate in 312. The difference failing to exceed the first threshold indicates the user is on track or target to reach the final breathing period at the non-linear prescribed rate. Method 300 may then restart at 304 to re-measure the current breathing period of the user.

If the difference does meet or exceed the first threshold, a determination is made at 314 as to whether the difference is a positive or negative value. The difference being a positive value indicates the user is leading the non-linear prescribed rate. If the difference is determined to be a positive value, the guided stimulus and the non-linear prescribed rate are decreased to re-align with the user's current breathing period at 316. The non-linear prescribed rate may be re-calculated to enable the user to reach the final breathing period in a shorter amount of time than originally calculated. Following 316, method 300 may restart at 304 to re-measure the current breathing period of the user.

If the difference is determined to be a negative value, method 300 proceeds to 318. The difference being a negative number indicates the user is lagging behind the entrainment sequence. In 318, a determination is made as to whether the difference between the target breathing period and the current breathing period meets or exceeds a second threshold. The second threshold is greater than the first threshold. The second threshold may be used only to determine how far behind the non-linear prescribed rate the user is lagging by, and may not be used to determine how far the user is leading by. Since a leading user is already predicted to reach the final breathing period, a determination regarding the second threshold need not be made. In one embodiment, the second threshold is about −1 seconds, indicating that the user is lagging by about 1 or more seconds.

If the difference meets or exceeds the first threshold but not the second threshold, the guided stimulus and the non-linear prescribed rate are stabilized at 320. The difference exceeding the first threshold but not the second threshold indicates the user is lagging behind the non-linear prescribed rate, but may still be able to re-align or catch back up to the current non-linear prescribed rate. Stabilizing the guided stimulus and the non-linear prescribed rate allows the current breathing period of the user to re-align to the guiding stimulus at the pace of the current non-linear prescribed rate. Following 320, method 300 may restart at 304 to re-measure the current breathing period of the user.

If the second threshold does meet or exceed the second threshold, the guided stimulus and the non-linear prescribed rate are increased at 322. The difference exceeding the second threshold indicates the user is grossly lagging behind the non-linear prescribed rate. The guided stimulus and the non-linear prescribed rate are increased to either align with the user's current breathing period to restart the user's entrainment, or to a rate that enables the user to re-align or catch up to a re-calculated non-linear prescribed rate. The re-calculated non-linear prescribed rate may be extended over a greater period of time, increasing the total entrainment period, or may be adjusted such that the user should reach the final breathing period in a quicker amount of time than originally set (i.e., steeper decreases of breaths per minute). Following 322, method 300 may restart at 304 to re-measure the current breathing period of the user.

Method 300 may restart one or more times until the user has reached the final breathing period. Once the user reaches the final breathing period, method 300 may end, and the guiding stimulus may stop being output. Furthermore, the entrainment system may react to non-respiration based feedback received from the biosensor. For example, if the system receives information indicating the user is asleep, the entrainment may be immediately stopped, or may be stopped gradually over time.

Table 1 illustrates an example embodiment of steps 310-322. In table 1, $\epsilon$ is the error or difference between the target breathing period and the current breathing period, and $\alpha$ represents the amount the non-linear prescribed rate should be adjust based on the determined difference.

TABLE 1

| Case | Description | Lagging/Leading | $\epsilon$ threshold | $\alpha$ period rise rate adjustment |
|---|---|---|---|---|
| 1 | User following sequence | On target | $\epsilon_{Lag1} < \epsilon < \epsilon_{Lead1}$ | $\alpha_1 > 0$ |
| 2 | User lagging beyond threshold | Lagging | $\epsilon_{Lag2} < \epsilon \leq \epsilon_{Lag1}$ | $\alpha_2 \approx 0$ |
| 3 | User grossly lagging sequence | Lagging | $\epsilon \leq \epsilon_{Lag2}$ | $\alpha_3 < 0$ |
| 4 | User leading sequence | Leading | $\epsilon_{Lead1} \leq \epsilon$ | $\alpha_4 > \alpha_1$ |

Case 1 in Table 1 illustrates an example of a user following the non-linear prescribed rate as intended. In case 1, when the difference or error was determined in 308 and compared to the first threshold in 310, the error was determined to be less than the first threshold and method 300 proceeded 312. The difference may be a positive or negative number. For instance, the difference or error of the user's current breathing rate was determined to be different than the target breathing period by between about −0.49 to 0.49 seconds. The difference being less than the first threshold indicates that the user is predicted to reach the final breathing period on target along the non-linear prescribed rate as originally calculated. As such, the guided stimulus is adjusted to continue following the non-linear proscribed rate.

Case 2 in Table 1 illustrates an example of a user lagging behind the non-linear prescribed rate. In case 2, the error was determined to meet or exceed the first threshold in 310 and to be a negative number in 314, but was determined not to meet or exceed the second threshold in 318. For instance, the difference or error of the user's current breathing rate was determined to be behind the target breathing period by between about −0.50 to −0.99 seconds. As such, the guided stimulus and the non-linear prescribed rate are stabilized to allow the user to re-align with the non-linear prescribed rate.

Case 3 in Table 1 illustrates an example of a user grossly lagging behind the non-linear prescribed rate. In case 3, the error was determined to exceed or meet the second threshold in 318. For instance, the difference or error of the user's current breathing rate was determined to be behind the target breathing period by about −1.00 seconds or greater. As such, the guided stimulus and the non-linear prescribed rate are increased to either align with the user's current breathing period to restart the user's entrainment, or to a rate that enables the user to re-align or catch up to a re-calculated non-linear prescribed rate. The re-calculated non-linear prescribed rate may be extended over a greater period of time, increasing the total entrainment period, or may be adjusted such that the user should reach the final breathing period in a quicker amount of time than originally set (i.e., steeper decreases of breaths per minute).

Case 4 in Table 1 indicates an example of a user leading ahead of the non-linear prescribed rate. In case 4, when the difference or error was determined in 308 and compared to the first threshold in 310, the error was determined to meet or exceed the first threshold in 310 and to be a positive number in 314. For instance, the difference or error of the user's current breathing rate was determined to be ahead of the target breathing period by about 0.50 seconds or greater. As such, the guided stimulus and the non-linear prescribed rate are decreased to re-align with the user's current breathing period. The non-linear prescribed rate may be re-calculated to enable the user to reach the final breathing period in a shorter amount of time than originally calculated.

The non-linear prescribed rate (α) may be calculated based on other parameters besides the error or difference (∈). For example, the non-linear prescribed rate may be adjusted based on the user's breathing period, the amount of time that has elapsed in entrainment, or the predetermined buffer time. Additionally, the non-linear prescribed rate may be adjusted based on one or more of the above parameters.

Moreover, the entrainment system may track how often the non-linear prescribed rate is adjusted. Long term tracking of the adjustments may enable an adaptive entrainment system that modulates its reactive parameters after going through an entrainment sequence. For example, tracking how many times the system must pause to let the user catch up can change how high the first threshold ($\alpha_1$) is. Lowering first threshold may minimize the need for the system to pause and can make the experience easier to follow for that user.

Figure 4:
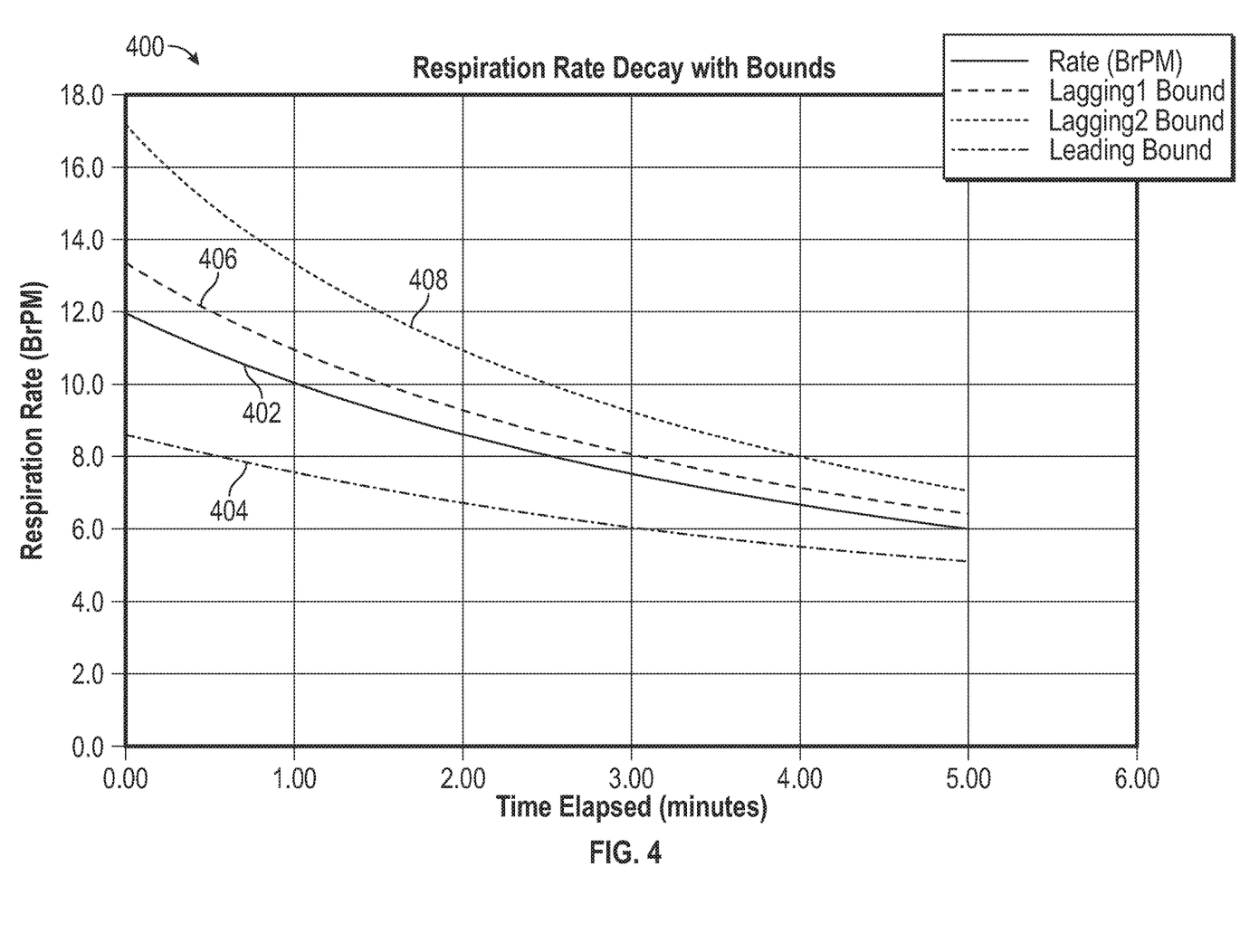
FIG. 4 illustrates a graph of an exemplary non-linear prescribed rate.

FIG. 4 illustrates a graph 400 of an exemplary non-linear prescribed rate 402. The graph 400 illustrates a respiration rate in breath rates per minute (BrPM) versus time elapsed in minutes. The graph 400 further illustrates exemplary bounds for a user leading 404 or lagging 406, 408 behind the exemplary non-linear prescribed rate 402. Line 402 illustrates the user being on target or on track with the non-linear prescribed rate 402, as described in case 1 of Table 1 above. Line 404 illustrates the user leading the non-linear prescribed rate 402, such as described in case 4 of Table 1 above. For example, line 404 illustrates the user leading the non-linear prescribed rate 402 by about 2 seconds. Line 406 illustrates the user lagging behind the non-linear prescribed rate 402, such as described in case 2 of Table 1 above. Line 406 illustrates the user lagging behind the non-linear prescribed rate 402 by about 0.5 seconds. Line 408 illustrates the user grossly lagging behind the non-linear prescribed rate 402, such as described in case 3 of Table 1 above. Line 408 illustrates the user grossly lagging behind the non-linear prescribed rate 402 by about 1.5 seconds.

Figure 5:
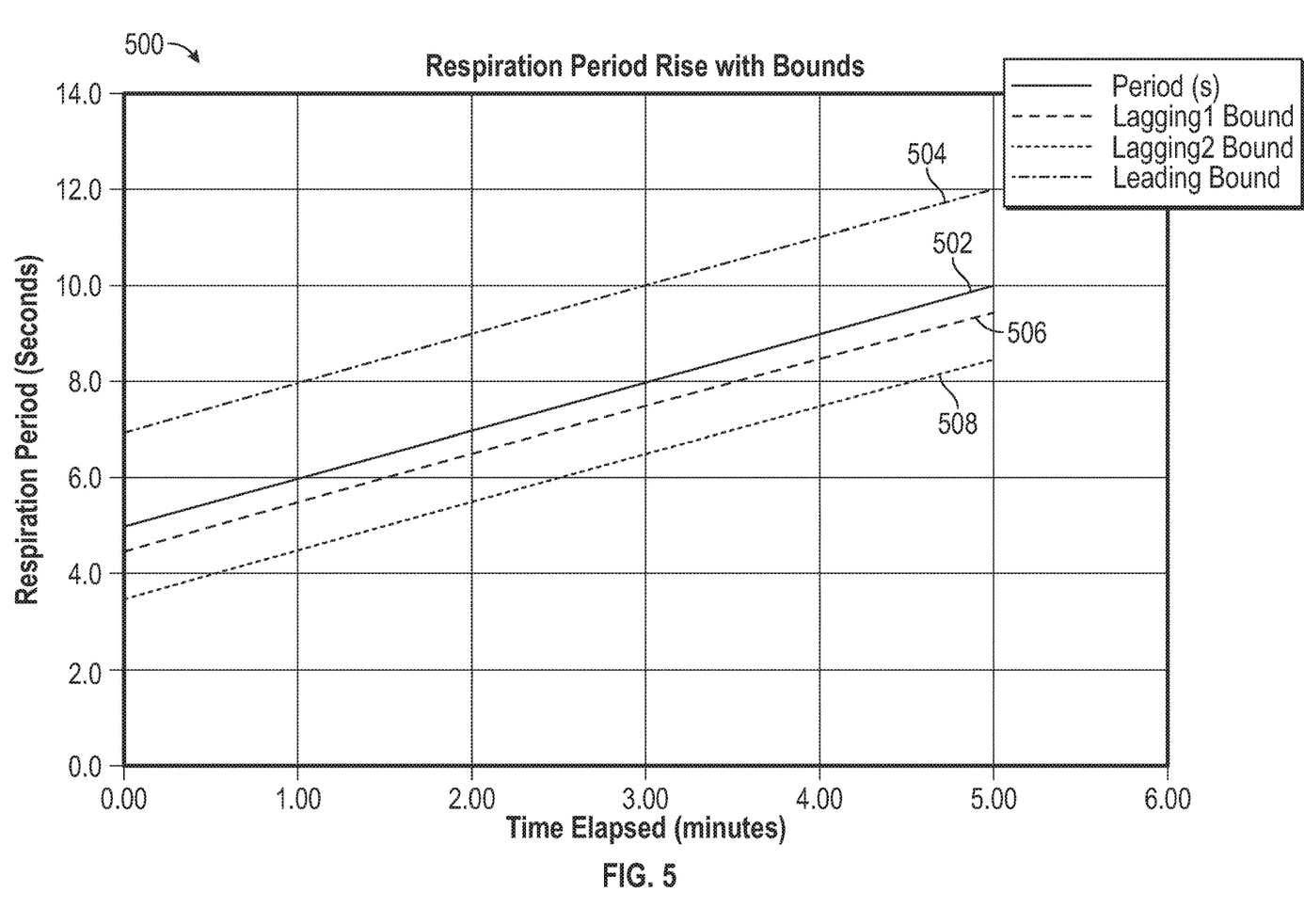
FIG. 5 illustrates a graph of an exemplary respiration period rise with bounds.

FIG. 5 illustrates a graph 500 of an exemplary respiration period rise with bounds. The graph 400 and graph 500 may be related such that the lines 402-408 of the graph 400 are the inverse of the lines 502-508 of the graph 500, respectively. The graph 500 includes a respiration period line 502. The slope of the respiration period line 502 is seconds of period rise per minute of entrainment. The slope of the respiration period line 502 may be adjusted by the value of α from Table 1 above (i.e., the amount the non-linear prescribed rate 402 of graph 400 should be adjusted based on the determined difference).

Similar to graph 400 of FIG. 4, the graph 500 further illustrates exemplary bounds for a user leading 504 or lagging 506, 508 behind the exemplary target respiration period line 502. Line 502 illustrates the user being on target or on track with the target respiration period line 502, as described in case 1 of Table 1 above. Line 504 illustrates the user leading the target respiration period line 502, such as described in case 4 of Table 1 above. For example, line 504 illustrates the user leading the target respiration period line 502 by about 2 seconds. Line 506 illustrates the user lagging behind the target respiration period line 502, such as described in case 2 of Table 1 above. Line 506 illustrates the user lagging behind the target respiration period line 502 by about 0.5 seconds. Line 508 illustrates the user grossly lagging behind the target respiration period line 502, such as described in case 3 of Table 1 above. Line 508 illustrates the user grossly lagging behind the target respiration period line 502 by about 1.5 seconds.

By measuring a current breathing period of a user and determining an error, if any, between the user's current breathing period and a target breathing period of where the user should be at along the non-linear prescribed rate, any errors may be taken into consideration and corrected to allow the user to reach the final breathing entrainment in a natural and comfortable manner. The logic of the entrainment system can be setup such that there is at least one threshold error value that affects other parts of the entrainment sequence, and the non-linear prescribed rate can be adjusted as needed. As such, users are more likely to complete the breathing entrainment sequence, and may complete the breathing entrainment in a more effective and quicker manner.

Aspects of the present disclosure provide methods, apparatuses, and systems for determining a difference between a current breathing period and a target breathing period along a non-linear prescribed rate. According to aspects, the audio device or system described herein is also configured to non-linearly alter a guiding stimulus with a non-linear breath rate per minute sequence to align with a final breathing period, as described in U.S. Patent Application Ser. No. 62/789,343 entitled "Non-Linear Breath Entrainment," filed on Jan. 7, 2019 (Docket No. WL-18-044-US) and International Application Number PCT/US2020/012349 entitled "Non-Linear Breath Entrainment," filed Jan. 6, 2020 (Docket No. WL-18-044-WO), which are hereby incorporated by reference in their entirety.

In the preceding, reference is made to aspects presented in this disclosure. However, the scope of the present disclosure is not limited to specific described aspects. Aspects of the present disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium include: an electrical connection having one or more wires, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain, or store a program.

The flowchart and block diagrams in the figures illustrate the architecture, functionality and operation of possible implementations of systems, methods and computer program products according to various aspects. In this regard, each block in the flowchart or block diagrams may represent a module, segment or portion of code, which comprises one or more executable instructions for implementing the specified logical function(s). In some implementations the functions noted in the block may occur out of the order noted in

The invention claimed is:

1. A method for breathing entrainment, comprising:
selecting a final breathing period, wherein a breathing period is an amount of time from a beginning of one inhale to an end of a next exhale;
measuring a current breathing period of a user;
outputting a guiding stimulus, wherein the guiding stimulus is configured to alter the current breathing period towards the final breathing period over an interval of time at a non-linear prescribed rate, the non-linear prescribed rate being a non-linear decay;
determining a difference between a target breathing period and the current breathing period, wherein the target breathing period is the breathing period the user should be at along the non-linear prescribed rate at a certain point of time; and
adjusting the guiding stimulus based at least in part on the difference between the target breathing period and the current breathing period.

2. The method of claim 1, wherein determining the difference between the target breathing period and the current breathing period comprises determining the difference exists for a predetermined amount of time prior to adjusting the guided stimulus.

3. The method of claim 1, wherein determining the difference between the target breathing period and the current breathing period comprises determining the difference exceeds a first threshold.

4. The method of claim 3, wherein the difference exceeding the first threshold indicates the current breathing period of the user is predicted to reach the final breathing period faster than the non-linear prescribed rate, and wherein the guiding stimulus and the non-linear prescribed rate are decreased to match the current breathing period of the user.

5. The method of claim 3, wherein the difference exceeding the first threshold indicates the current breathing period of the user is predicted to reach the final breathing period slower than the non-linear prescribed rate, and wherein the guiding stimulus and the non-linear prescribed rate are stabilized to allow the current breathing period of the user to align to the guiding stimulus and the non-linear prescribed rate.

6. The method of claim 3, further comprising:
determining the difference between the target breathing period and the current breathing period exceeds a second threshold greater than the first threshold, wherein the difference exceeding the second threshold indicates the current breathing period of the user is predicted to reach the final breathing period slower than the non-linear prescribed rate, and wherein the guiding stimulus and the non-linear prescribed rate are increased to match the current breathing period of the user.

7. The method of claim 1, further comprising:
determining the difference between the target breathing period and the current breathing period does not exceed a first threshold, wherein the guided stimulus is adjusted at the non-linear prescribed rate.

8. A wearable audio device, comprising:
at least one biosensor for measuring a current breathing period of a user wearing the wearable audio device, wherein a breathing period is an amount of time from a beginning of one inhale to an end of a next exhale;
at least one speaker configured to output a guiding stimulus, wherein the guiding stimulus is configured to alter the current breathing period towards a final breathing period over an interval of time at a non-linear prescribed rate, the non-linear prescribed rate being a non-linear decay; and
a processing unit configured to:
select the final breathing period;
determine a difference between a target breathing period and the current breathing period, wherein the target breathing period is the breathing period the user should be at along the non-linear prescribed rate at a certain point of time; and
adjust the guiding stimulus based at least in part on the difference between the target breathing period and the current breathing period.

9. The wearable audio device of claim 8, wherein the processing unit is further configured to determine the difference exists for a predetermined amount of time prior to adjusting the guided stimulus.

10. The wearable audio device of claim 8, wherein the processing unit is further configured to determine the difference exceeds a first threshold.

11. The wearable audio device of claim 10, wherein the difference exceeding the first threshold indicates the current breathing period of the user is predicted to reach the final breathing period faster than the non-linear prescribed rate, and wherein the guiding stimulus and the non-linear prescribed rate are decreased to match the current breathing period of the user.

12. The wearable audio device of claim 10, wherein the difference exceeding the first threshold indicates the current breathing period of the user is predicted to reach the final breathing period slower than the non-linear prescribed rate, and wherein the guiding stimulus and the non-linear prescribed rate are stabilized to allow the current breathing period of the user to align to the guiding stimulus and the non-linear prescribed rate.

13. The wearable audio device of claim 10, wherein the processing unit is further configured to determine the difference between the target breathing period and the current breathing period exceeds a second threshold greater than the first threshold, wherein the difference exceeding the second threshold indicates the current breathing period of the user is predicted to reach the final breathing period slower than the non-linear prescribed rate, and wherein the guiding stimulus and the non-linear prescribed rate are increased to match the current breathing period of the user.

14. The wearable audio device of claim 8, wherein the processing unit is further configured to determine the difference between the target breathing period and the current breathing period does not exceed a first threshold, wherein the guided stimulus is adjusted at the non-linear prescribed rate.

15. An audio system, comprising:
at least one biosensor for measuring a current breathing period of a user, wherein a breathing period is an amount of time from a beginning of one inhale to an end of a next exhale;

at least one speaker configured to output a guiding stimulus, wherein the guiding stimulus is configured to alter the current breathing period towards a final breathing period over an interval of time at a non-linear prescribed rate, the non-linear prescribed rate being a non-linear decay; and a processing unit configured to:
 select the final breathing period;
 determine a difference between a target breathing period and the current breathing period, wherein the target breathing period is the breathing period the user should be at along the non-linear prescribed rate at a certain point of time; and
 adjust the guiding stimulus based at least in part on the difference between the target breathing period and the current breathing period.

16. The audio system of claim 15, wherein the processing unit is further configured to determine the difference exists for a predetermined amount of time prior to adjusting the guided stimulus.

17. The audio system of claim 15, wherein the processing unit is further configured to determine the difference exceeds a first threshold.

18. The audio system of claim 17, wherein the difference exceeding the first threshold indicates the current breathing period of the user is predicted to reach the final breathing period faster than the non-linear prescribed rate, and wherein the guiding stimulus and the non-linear prescribed rate are decreased to match the current breathing period of the user.

19. The audio system of claim 17, wherein the difference exceeding the first threshold indicates the current breathing period of the user is predicted to reach the final breathing period slower than the non-linear prescribed rate, and wherein the guiding stimulus and the non-linear prescribed rate are stabilized to allow the current breathing period of the user to align to the guiding stimulus and the non-linear prescribed rate.

20. The audio system of claim 17, wherein the processing unit is further configured to determine the difference between the target breathing period and the current breathing period exceeds a second threshold greater than the first threshold, wherein the difference exceeding the second threshold indicates the current breathing period of the user is predicted to reach the final breathing period slower than the non-linear prescribed rate, and wherein the guiding stimulus and the non-linear prescribed rate are increased to match the current breathing period of the user.

21. The audio system of claim 15, wherein the processing unit is further configured to determine the difference between the target breathing period and the current breathing period does not exceed a first threshold, wherein the guided stimulus is adjusted at the non-linear prescribed rate.

* * * * *